United States Patent
Torashima et al.

(10) Patent No.: US 9,955,949 B2
(45) Date of Patent: May 1, 2018

(54) METHOD FOR MANUFACTURING A CAPACITIVE TRANSDUCER

(71) Applicant: CANON KABUSHIKI KAISHA, Tokyo (JP)

(72) Inventors: Kazutoshi Torashima, Yokohama (JP); Takahiro Akiyama, Kawasaki (JP); Kenji Hasegawa, Kawasaki (JP); Kazuhiko Kato, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 551 days.

(21) Appl. No.: 14/463,420

(22) Filed: Aug. 19, 2014

(65) Prior Publication Data
US 2015/0057547 A1 Feb. 26, 2015

(30) Foreign Application Priority Data

Aug. 23, 2013 (JP) .................................. 2013-173190
Sep. 8, 2013 (JP) .................................. 2013-185796

(51) Int. Cl.
*H04R 31/00* (2006.01)
*A61B 8/00* (2006.01)
(Continued)

(52) U.S. Cl.
CPC .......... *A61B 8/4494* (2013.01); *A61B 5/0095* (2013.01); *B06B 1/0292* (2013.01);
(Continued)

(58) Field of Classification Search
CPC ... A61B 5/0095; A61B 8/4483; A61B 8/4494; B06B 1/0292; B81C 1/00182;
(Continued)

(56) References Cited

U.S. PATENT DOCUMENTS 7,790,490 B2 * 9/2010 Caliano ................. B06B 1/0292
                                                 257/E21.214
8,288,192 B2 * 10/2012 Chang ................... B06B 1/0292
                                                 257/419
(Continued)

FOREIGN PATENT DOCUMENTS

CN       102336392 A    2/2012
CN       102728535 A    10/2012
(Continued)

*Primary Examiner* — Paul D Kim
(74) *Attorney, Agent, or Firm* — Canon U.S.A., Inc. IP Division

(57) ABSTRACT

A method for manufacturing a capacitive transducer is provided having a structure in which a vibrating film is supported to be able to vibrate. The method includes forming a sacrificial layer on a first electrode; forming a layer on the sacrificial layer, the layer forming at least part of the vibrating film; removing the sacrificial layer, including forming etching holes to communicate with the sacrificial layer; forming a sealing layer for sealing the etching holes; and etching at least part of the sealing layer. Before forming the sealing layer, an etching stop layer is formed on the layer forming at least part of the vibrating film. In the step of etching at least part of the sealing layer, the sealing layer is removed until the etching stop layer is reached.

15 Claims, 9 Drawing Sheets

(51) Int. Cl.
B06B 1/02 (2006.01)
B81C 1/00 (2006.01)
A61B 5/00 (2006.01)
H02N 1/08 (2006.01)

(52) U.S. Cl.
CPC .......... B81C 1/00182 (2013.01); H02N 1/08 (2013.01); *B81B 2201/0271* (2013.01)

(58) Field of Classification Search
CPC .................. H02N 1/08; B81B 2201/0271; C23C 16/513; C23C 16/345; C23C 16/401
See application file for complete search history.

(56) References Cited

U.S. PATENT DOCUMENTS

| | | | | |
|---|---|---|---|---|
| 8,760,035 B2 * | 6/2014 | Tomiyoshi | ............ | B06B 1/0292 310/322 |
| 2005/0177045 A1 * | 8/2005 | Degertekin | ........ | G01N 29/2406 600/457 |
| 2011/0086443 A1 | 4/2011 | Kobayashi | | |
| 2011/0305822 A1 | 12/2011 | Hasegawa | | |
| 2012/0256518 A1 * | 10/2012 | Torashima | ............ | B06B 1/0292 310/300 |
| 2013/0069480 A1 * | 3/2013 | Akiyama | ............... | H02N 11/00 310/300 |
| 2015/0366539 A1 * | 12/2015 | Hasegawa | ............ | B06B 1/0292 600/459 |

FOREIGN PATENT DOCUMENTS

| | | |
|---|---|---|
| JP | 2007-528153 A | 10/2007 |
| JP | 2008-098697 A | 4/2008 |
| JP | 2011-244425 A | 12/2011 |
| JP | 2011-259371 A | 12/2011 |
| JP | 2012-227950 A | 11/2012 |

* cited by examiner

METHOD FOR MANUFACTURING A CAPACITIVE TRANSDUCER

BACKGROUND OF THE INVENTION

Field of the Invention

The present invention relates to a capacitive transducer used as an ultrasonic electromechanical transducer or the like, and also relates to a method for manufacturing the capacitive transducer.

Description of the Related Art

Micromechanical members manufactured by micromachining can be processed in the order of micrometers. Various micro-functional devices are implemented by such micromechanical members. Capacitive transducers using such technology have been studied as substitutes for piezoelectric devices. Such a capacitive transducer is capable of transmitting and receiving acoustic waves, such as ultrasonic waves, by using vibration of a vibrating film (acoustic waves may be hereinafter referred to as ultrasonic waves). The capacitive transducer can easily achieve good wideband characteristics particularly in liquid. As used herein, the term "acoustic waves" includes those referred to as sonic waves, ultrasonic waves, and photoacoustic waves. For example, the term "acoustic waves" includes photoacoustic waves generated in a subject by irradiating the inside of the subject with visible light or infrared light (electromagnetic waves).

Japanese Patent Laid-Open No. 2008-98697 proposes a capacitive transducer related to the technology described above. This capacitive transducer is made by removing a sacrificial layer by means of wet etching through etching holes, and performing filling-up sealing which involves sealing the etching holes with an insulating film. PCT Japanese Translation Patent Publication No. 2007-528153 discloses another capacitive transducer. This capacitive transducer is made by removing a sacrificial layer by means of wet etching through etching holes, performing filling-up sealing which involves sealing the etching holes with an insulating film, and then etching the insulating film, so that the thickness of a vibrating film can be adjusted to achieve desired resonance frequencies.

In the configuration disclosed in Japanese Patent Laid-Open No. 2008-98697, the entire thickness of a layer for filling-up sealing of the etching holes used to remove the sacrificial layer is added to the thickness of the vibrating film. This increases the thickness of the vibrating film and narrows the frequency band accordingly.

With the technique disclosed in PCT Japanese Translation Patent Publication No. 2007-528153, a capacitive transducer having a wide frequency band can be made by forming a thin vibrating film. However, reducing the thickness of the vibrating film by means of etching may cause variation in the thickness of the vibrating film due to variation in etching rate in the substrate. This leads to variation in frequency characteristics and transmission and reception sensitivity of the capacitive transducer.

A thin vibrating film tends to deform significantly under stress or depending on the thickness. Since this makes it difficult to create a narrow gap, it is not easy to improve the sensitivity of the capacitive transducer.

SUMMARY OF THE INVENTION

The present invention provides a capacitive transducer having a thin vibrating film with reduced thickness variation.

To solve the problems described above, the present invention provides a method for manufacturing a capacitive transducer including a cell having a structure in which a vibrating film including a second electrode disposed across a gap from a first electrode is supported to be able to vibrate. The method includes the steps of forming a sacrificial layer on the first electrode; forming a layer on the sacrificial layer, the layer forming at least part of the vibrating film; removing the sacrificial layer, including forming etching holes to communicate with the sacrificial layer; forming a sealing layer for sealing the etching holes; and etching at least part of the sealing layer. Before the step of forming the sealing layer, an etching stop layer is formed on the layer forming at least part of the vibrating film. In the step of etching at least part of the sealing layer, the sealing layer is removed until the etching stop layer is reached.

The present invention also provides a capacitive transducer including a cell having a structure in which a vibrating film including a second electrode disposed across a gap from a first electrode is supported to be able to vibrate. The vibrating film includes a first membrane and a second membrane disposed with the second electrode interposed therebetween. The center plane in the direction of thickness (hereinafter simply referred to as a "center plane") of a layer having the highest stress among the first membrane, the second membrane, and the second electrode is located closer to the gap than a center plane of the vibrating film is to the gap.

Further features of the present invention will become apparent from the following description of exemplary embodiments with reference to the attached drawings.

DESCRIPTION OF THE EMBODIMENTS

First Embodiment

In a method for manufacturing a capacitive transducer according to a first embodiment of the present invention, a capacitive transducer is made which includes a cell having a structure in which a vibrating film including a second electrode disposed across a gap from a first electrode is supported to be able to vibrate. With this method, the capacitive transducer can be made easily and variation in thickness of the vibrating film can be reduced. In this method, after a layer forming at least part of the vibrating film is formed on a sacrificial layer on a first electrode, an etching stop layer is formed on the layer forming at least part of the vibrating film, and then the sacrificial layer is removed by forming etching holes. After a sealing layer for sealing the etching holes is formed, the sealing layer is removed until the etching stop layer is reached. The first embodiment and examples of the present invention will now be described on the basis of the ideas described above. However, the present invention is not limited to the first embodiment and examples, and may be variously modified and changed within the scope of the gist of the present invention.

Figure 1A:
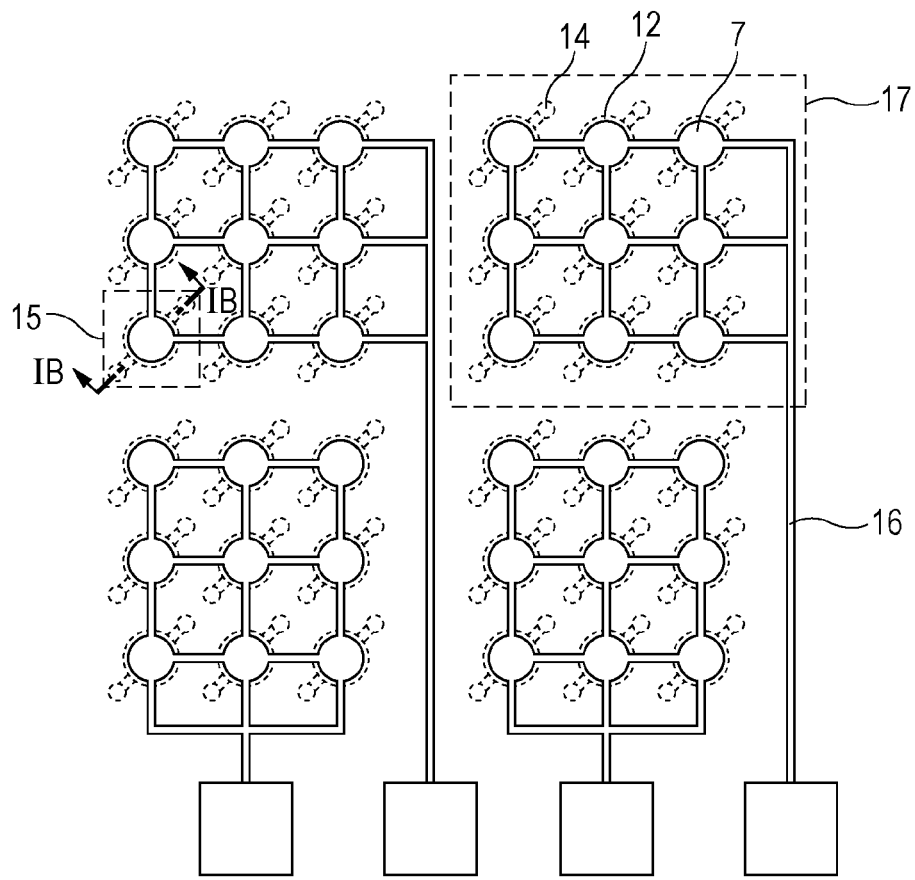
FIG. 1A is a top view of a capacitive transducer according to a first embodiment of the present invention.
Figure 1B:
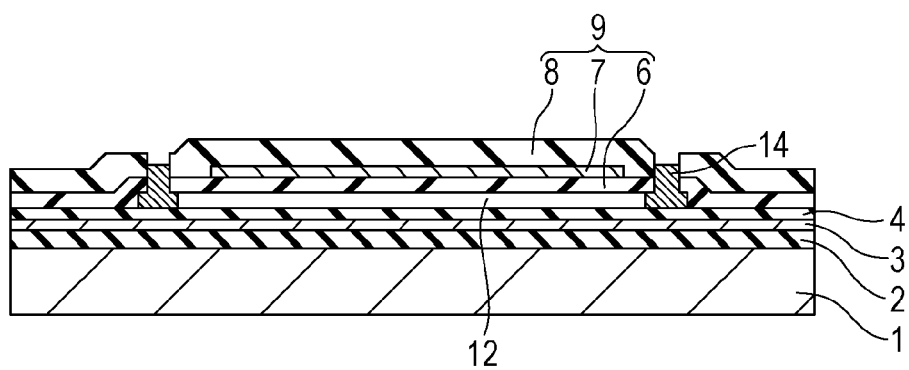
FIG. 1B is a cross-sectional view taken along line IB-IB of FIG. 1A.

The first embodiment of the present invention will be described with reference to FIGS. 1A and 1B and FIGS. 2A to 2H. FIG. 1A is a top view of a capacitive transducer. FIG. 1B is a cross-sectional view taken along line IB-IB of FIG. 1A. FIGS. 2A to 2H are cross-sectional views corresponding to FIG. 1B and illustrating steps of a method for manufacturing the capacitive transducer illustrated in FIGS. 1A and 1B.

The capacitive transducer made by the method of the first embodiment has elements 17 each including a plurality of cells 15. Each element 17 includes nine cells 15 in FIG. 1A, but may include any number of cells. The capacitive transducer illustrated in FIG. 1A includes four elements 17, but may include any number of elements.

In each cell 15, a vibrating film 9 (see FIG. 1B) including a second electrode 7 disposed across a gap 12 from a first electrode 3 is supported to be able to vibrate. The vibrating film 9 in FIG. 1B includes a first membrane 6, a second membrane 8, and the second electrode 7 interposed therebetween, but the vibrating film 9 may have any configuration as long as it can vibrate and includes the second electrode 7. For example, the vibrating film 9 may include the second electrode 7 alone, or one of the first and second membranes 6 and 8 and the second electrode 7 alone. One of the first and second electrodes 3 and 7 is used as an electrode for applying a bias voltage, and the other is used as an electrode for applying or outputting an electrical signal. The first electrode 3 is used as an electrode for applying a bias voltage and the second electrode 7 is used as a signal output electrode in FIGS. 1A and 1B, but this may be reversed. The electrode for applying a bias voltage is common in each element 17. The bias voltage may be common among the plurality of elements 17, but the signal output electrode needs to be electrically separated for each element 17.

A driving principle of the first embodiment will now be described. With a signal lead wire 16, the capacitive transducer can transmit an electrical signal from the second electrode 7. An electrical signal is transmitted through the signal lead wire 16 in the first embodiment, but may be transmitted through a through wire. An electrical signal is transmitted from the second electrode 7 in the first embodiment, but may be transmitted from the first electrode 3. For the capacitive transducer to receive ultrasonic waves, a voltage applying unit (not shown) applies a direct-current voltage to the first electrode 3 in advance. When ultrasonic waves are received, the vibrating film 9 including the second electrode 7 deforms. This changes the distance of the gap 12 between the second electrode 7 and the first electrode 3 and changes the capacitance therebetween. The change in capacitance causes current to flow through the signal lead wire 16. This current is converted by a current-to-voltage converter (not shown) to a voltage, so that ultrasonic waves can be received. The configuration of the signal lead wire 16 may be changed to apply a direct-current voltage to the second electrode 7 and output an electrical signal from the first electrode 3. When an alternating voltage is applied to the second electrode 7, the resulting electrostatic force causes the vibrating film 9 to vibrate. This allows transmission of ultrasonic waves. For transmission, the configuration of the signal lead wire 16 may be changed to apply an alternating voltage to the first electrode 3 and cause the vibrating film 9 to vibrate.

Figure 2A:
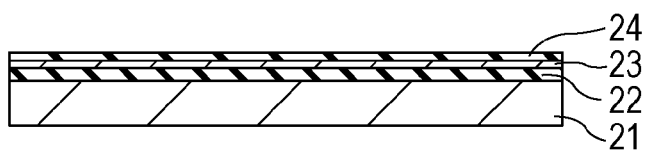
FIGS. 2A to 2H are cross-sectional views corresponding to FIG. 1B and illustrating a method for manufacturing the capacitive transducer illustrated in FIGS. 1A and 1B.

A method for manufacturing the capacitive transducer of the first embodiment will now be described. FIGS. 2A to 2H each correspond to the cross-sectional view taken along line IB-IB of FIG. 1A. As illustrated in FIG. 2A, a first insulating film 22 (corresponding to a first insulating film 2 in FIG. 1B) is formed on a substrate 21 (corresponding to a substrate 1 in FIG. 1B). The substrate 21 is a silicon substrate. The first insulating film 22 on the substrate 21 is provided for insulation between the silicon substrate 21 and a first electrode 23 (described below). If the substrate 21 is an insulating substrate, such as a glass substrate, the first insulating film 22 on the substrate 21 may not be provided. The substrate 21 may be a substrate with small surface roughness. If the substrate 21 has large surface roughness, the surface roughness is transferred in the subsequent film deposition step, and causes variation in distance between the first electrode 23 and a second electrode 27 (described below) among cells and elements. This variation leads to variation in transmission and reception sensitivity. Therefore, a substrate with small surface roughness may be used as the substrate 21.

Next, the first electrode 23 (corresponding to the first electrode 3 in FIG. 1B) is formed. The first electrode 23 may be made of a conductive material, such as titanium or aluminum, that provides small surface roughness. As in the case of the substrate 21, if the first electrode 23 has large surface roughness, the surface roughness causes variation in distance between the first electrode 23 and the second electrode 27 among cells and elements. Therefore, the first electrode 23 made of a conductive material that provides small surface roughness may be used. Next, a second insulating film 24 (corresponding to a second insulating film 4 in FIG. 1B) is formed. The second insulating film 24 on the first electrode 23 may be made of a non-conductive material that provides small surface roughness. The second insulating film 24 is formed to prevent an electrical short circuit or dielectric breakdown between the first electrode 23 and the second electrode 27 when a voltage is applied therebetween. When the capacitive transducer is driven at a low voltage, the second insulating film 24 may not be provided if a first membrane 26 (described below) is an insulator. The second insulating film 24 is formed on the first electrode 23 to prevent the first electrode 23 from being etched in an etching step of etching a sacrificial layer 25 (described below). As in the case of the substrate 21, if the second insulating film 24 has large surface roughness, the surface roughness causes variation in distance between the first electrode 23 and the second electrode 27 among cells and elements. Therefore, an insulating film with small surface roughness may be used as the second insulating film 24. For example, the second insulating film 24 may be a silicon nitride film or a silicon oxide film.

Figure 2B:
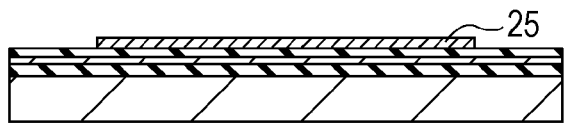

Next, the sacrificial layer 25 is formed as illustrated in FIG. 2B. The sacrificial layer 25 may be made of a material that provides small surface roughness. As in the case of the substrate 21, if the sacrificial layer 25 has large surface roughness, the surface roughness causes variation in distance between the first electrode 23 and the second electrode 27 among cells and elements. Therefore, the sacrificial layer 25 may have small surface roughness. To shorten the time of etching for removing the sacrificial layer 25, a material having a high etching rate may be used to form the sacrificial layer 25. Layers to be in contact with an etching solution or gas for removing the sacrificial layer 25 may be barely etched with this etching solution or gas. In FIGS. 2A to 2H, the layers to be in contact with this etching solution or gas include the second insulating film 24 on the first electrode 23, a first membrane 26 (corresponding to the first membrane 6 illustrated in FIG. 1B), etching holes 31, and an etching stop layer 30 (described below). When the second insulating film 24 on the first electrode 23 and the first membrane 26 are almost entirely etched with the etching solution or gas for removing the sacrificial layer 25, the thickness of the vibrating film 29 and the distance between the first electrode 23 and the second electrode 27 vary. The variation in thickness of the vibrating film 29 and the variation in distance between the first electrode 23 and the second electrode 27 lead to variation in sensitivity among cells and elements. When the second insulating film 24 on the first electrode 23 and the first membrane are each a silicon nitride film or a silicon oxide film, the sacrificial layer 25 may be made of chromium that provides small surface roughness and can be etched with an etching solution with which the second insulating film 24 on the first electrode 23 and the first membrane are not etched.

Figure 2C:
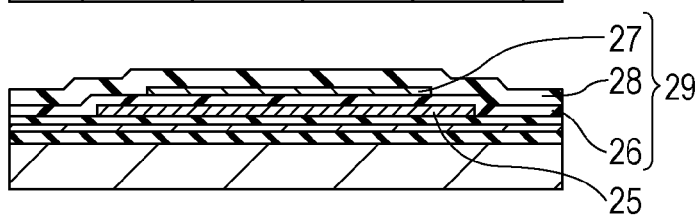

Next, the first insulating layer 26 including a first membrane is formed as illustrated in FIG. 2C. The first insulating layer 26 may have a low tensile stress. For example, the tensile stress of the first insulating layer 26 may be 300 MPa or less. A silicon nitride film is stress-controllable and can be formed to have a low tensile stress of 300 MPa or less. If the first insulating layer 26 has a compressive stress, the vibrating film 29 may be significantly deformed by sticking or buckling. Sticking refers to adhesion of the vibrating film 29, which is a structural body, after removal of the sacrificial layer 25. In the case of a high tensile stress, the vibrating film 29 may be broken. Therefore, the first insulating layer 26 may have a low tensile stress.

Next, a second electrode 27 (corresponding to the second electrode 7 in FIGS. 1A and 1B) is formed. The second electrode 27 may have a low residual stress and may be made of a material having high heat resistance. The second electrode 27 having a low residual stress may be used, because a high residual stress of the second electrode 27 causes significant deformation of the vibrating film 29. The material of the second electrode 27 may be one that does not cause any alteration or increase in stress depending on, for example, the temperature for depositing a second insulating layer 28 including the second membrane or a sealing layer 33 for forming sealing portions 34. For example, the second electrode 27 may be made of titanium or aluminum-silicon alloy.

Next, the second insulating layer 28 including the second membrane is formed. The second insulating layer 28 may be made of a material having a low tensile stress. As in the case of the first insulating layer 26, if the second insulating layer 28 has a compressive stress, the vibrating film 29 may be significantly deformed by sticking or buckling. In the case of a high tensile stress, the vibrating film 29 may be broken. Therefore, the second insulating layer 28 may have a low tensile stress. A silicon nitride film is stress-controllable and can be formed to have a low tensile stress of 300 MPa or less. Although the vibrating film 29 includes the first membrane, the second electrode 27, and the second membrane in FIG. 2C, the vibrating film 29 may include any number of layers as long as it includes the second electrode 27. The second electrode 27 may also serve as a membrane, and the vibrating film 29 may be formed by the second electrode 27 alone.

Figure 2D:
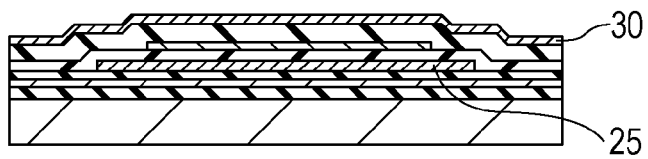

Next, as illustrated in FIG. 2D, the etching stop layer 30 is formed on the vibrating film 29 formed by deposition. The etching stop layer 30 is formed to make the vibrating film 29 have a desired thickness. The etching stop layer 30 is left to prevent the vibrating film 29 from being etched while a sealing material is being etched in a sealing layer removing step illustrated in FIG. 2G. In a sacrificial layer removing step (described below) illustrated in FIG. 2E, the etching stop layer 30 needs to be left when being in contact with the solution or gas for etching the sacrificial layer 25. Therefore, the etching stop layer 30 may be made of a material etched with the solution or gas for etching the sealing material at an etching rate lower than that at which the sealing material is etched. When the etching stop layer 30 is in contact with the solution or gas for etching the sacrificial layer 25 in the sacrificial layer removing step, the etching stop layer 30 may be made of a material etched with the solution or gas for etching the sacrificial layer material at an etching rate lower than that at which the sacrificial layer material is etched. To leave the etching stop layer 30 unremoved during etching, a material different from the vibrating film material may be made thicker. If the vibrating film 29 is a silicon nitride film and the sacrificial layer 25 is a chrome layer, an insulating film, such as a silicon oxide film, may be used as the etching stop layer 30. If the vibrating film 29 is a silicon nitride film and the sacrificial layer 25 is a silicon layer, such as a polysilicon or amorphous silicon layer, the etching stop layer 30 may be an insulating film, such as a silicon oxide film, or a metal film. If the vibrating film 29 is a silicon nitride film and the sacrificial layer 25 is a silicon oxide layer, the etching stop layer 30 may be a silicon film or a metal film. The etching stop layer 30, which is formed to determine the thickness of the vibrating film 29, may be formed at least on the vibrating film 29.

Figure 2E:
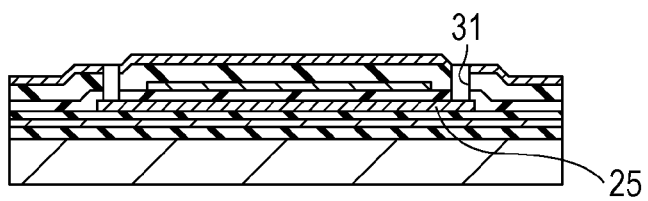

Next, the etching holes 31 are formed as illustrated in FIG. 2E. The etching holes 31 are for introducing an etching solution or gas for removing the sacrificial layer 25. When the etching stop layer 30 is formed on the entire surface of a thin film including the vibrating film 29, the etching holes 31 pass through the etching stop layer 30 and the thin film. Next, the sacrificial layer 25 is removed to form a gap 32 (corresponding to the gap 12 in FIGS. 1A and 1B). The sacrificial layer 25 may be removed by wet etching or dry etching.

Figure 2F:
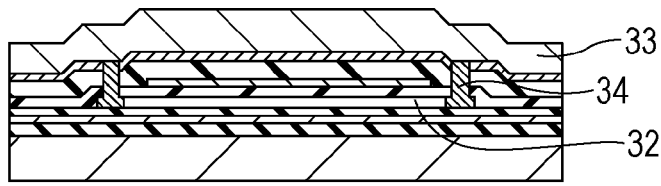

Next, as illustrated in FIG. 2F, the sealing layer 33 is formed to form sealing portions 34 (corresponding to sealing portions 14 in FIGS. 1A and 1B) for sealing the etching holes 31. The sealing portions 34 are configured to prevent entry of liquid and outside air into the gap 32. Particularly when the etching holes 31 are sealed under reduced pressure, the vibrating film 29 is deformed by atmospheric pressure and the distance between the first electrode 23 and the second electrode 27 is shortened. The transmission or reception sensitivity is inversely proportional to the 1.5th power of the effective distance between the first electrode 23 and the second electrode 27. Therefore, when the etching holes 31 are sealed under reduced pressure and the pressure in the gap 32 is kept lower than the atmospheric pressure, the transmission or reception sensitivity can be improved. Sealing the etching holes 31 allows the capacitive transducer to be used in liquid. For better adhesion, the sealing material may be the same as the material of the vibrating film 29. Since conformal deposition is less likely to occur by plasma-enhanced chemical vapor deposition (PECVD), good sealing portions 34 can be obtained by forming the sealing layer 33 of small thickness. When the vibrating film 29 is a silicon nitride film, the vibrating film 29 may be formed by PECVD of silicon nitride.

Figure 2G:
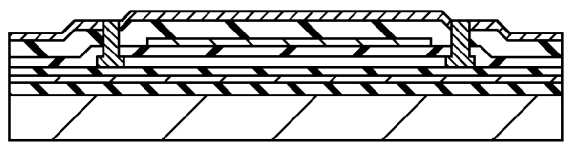

Next, as illustrated in FIG. 2G, the sealing layer 33 is removed until the etching stop layer 30 is reached. The etching stop layer 30 is sufficiently thick or is etched with the solution or gas for etching the sealing layer 33 at an etching rate lower than that at which the sealing layer 33 is etched. Therefore, even when the sealing layer 33 is etched for a period of time longer than a predetermined etching period for removing the sealing layer 33 until the etching stop layer 30 is reached, the sealing layer 33 can be removed without etching the vibrating film 29. Therefore, as compared to the case where no etching stop layer is provided, variation in thickness of the vibrating film 29 can be reduced even if the etching rate for removing the sealing layer 33 varies in the substrate 21. Thus, it is easy to control the thickness of the vibrating film 29 and possible to reduce variation in spring constant of the vibrating film 29 or variation in deformation of the vibrating film 29 caused by variation in thickness of the vibrating film 29. It is thus possible to reduce variation in reception or transmission sensitivity among cells or elements. Although the etching stop layer 30 is not present on the sealing portions 34, since the sealing portions 34 are as small as several micrometers, the sealing portions 34 are etched at a very low rate and do not leak even when the sealing layer 33 is etched for a period of time longer than the predetermined etching period.

Figure 2H:
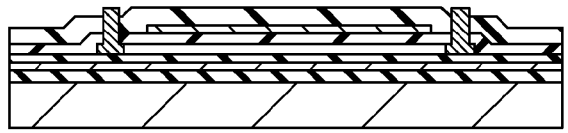

Next, the etching stop layer 30 is removed as illustrated in FIG. 2H. The vibrating film 29 including the first insulating layer 26, the second electrode 27, and the second insulating layer 28 is thus obtained. The etching stop layer 30 may be left and used as the vibrating film 29. In another step (not shown), a wire connected to the first electrode 23 and the second electrode 27 is formed. The wire may be made of aluminum.

In the present method for manufacturing a capacitive transducer, where a sealing layer can be removed, a thin vibrating film can be obtained. The capacitive transducer including the thin vibrating film can have a very wide frequency band. The vibrating film can be formed by a film deposition step alone. This means that it is easy to control the thickness of the vibrating film and possible to reduce variation in spring constant of the vibrating film or variation in deformation of the vibrating film caused by variation in thickness of the vibrating film. Therefore, it is possible to reduce variation in reception or transmission sensitivity among cells or elements.

Also, the present method can be used as a method for manufacturing a capacitive transducer that includes a vibrating film having a first membrane and a second membrane disposed with a second electrode interposed therebetween. The capacitive transducer may be made such that a center plane of a layer having the highest stress among a first insulating layer, a second insulating layer, and a metal layer (second electrode) is located closer to the gap (i.e., first electrode) than a center plane of the vibrating film is to the gap. When the center plane of the layer having the highest stress is located closer to the gap than the center plane of the vibrating film is to the gap, it is possible to reduce a bending moment acting on a fixed portion (or support portion) of the vibrating film, and thus to reduce deformation of the vibrating film. Therefore, it is possible to prevent sticking from occurring when a sacrificial layer is removed with an etching solution. Sticking refers to adhesion of the vibrating film, which is a structural body, after removal of the sacrificial layer. Since sticking depends on the surface tension of liquid, such as an etching solution, in the gap and the distance of the gap, sticking becomes more likely to occur as the degree of deformation of the vibrating film increases. When the stress of the vibrating film is a compressive stress, the vibrating film may be formed into a large convex shape (protruding in the direction opposite the first electrode). Since the transmission or reception sensitivity is inversely proportional to the 1.5th power of the effective distance between the first electrode and the second electrode, the transmission or reception sensitivity may be lowered if the vibrating film has a large convex shape. The present method for manufacturing the capacitive transducer can reduce deformation of the vibrating film, and thus can prevent degradation of the transmission or reception sensitivity.

The capacitive transducer may be made such that the vibrating film has a tensile stress and the etching stop layer has a compressive stress. With this configuration, the vibrating film having a tensile stress and the etching stop layer having a compressive stress can reduce deformation of a structure including the vibrating film and the etching stop layer when the sacrificial layer is removed. It is thus possible to prevent sticking of the structure including the vibrating film and the etching stop layer when the sacrificial layer is removed.

In the capacitive transducer of the first embodiment, a center plane of a layer having the highest stress among the first membrane, the second membrane, and the second electrode is located closer to the gap than the center plane of the vibrating film is to the gap. With this configuration, it is possible to reduce a difference in the amount of deformation in each vibrating film caused by variation in thickness and stress of the first membrane, the second membrane, and the second electrode included in the vibrating film. It is thus possible to reduce variation in frequency characteristics and transmission and reception sensitivity of the capacitive transducer.

The first embodiment will be described in detail using concrete examples.

Example 1

Example 1 will be described with reference to FIGS. 1A and 1B. The capacitive transducer of Example 1 has elements 17 each including a plurality of cells 15. Each element 17 includes nine cells 15 in FIG. 1A, but may include any number of cells. The capacitive transducer illustrated in FIG. 1A includes four elements 17, but may include any number of elements.

In each cell 15, the vibrating film 9 including the second electrode 7 disposed across the gap 12 from the first electrode 3 is supported to be able to vibrate. The vibrating film 9 includes the first membrane 6, the second membrane 8, and the second electrode 7 interposed therebetween. The first electrode 3 serves as an electrode for applying a bias voltage, and the second electrode 7 serves as a signal output electrode. Although the vibrating film 9 of Example 1 is circular in shape, it may be rectangular or hexagonal in shape. In the case of a circular shape, the vibrating film 9 vibrates in an axisymmetric vibration mode. It is thus possible to reduce vibration of the vibrating film 9 in an unnecessary vibration mode.

The first insulating film 2 on the silicon substrate 1 is a 1-µm-thick silicon oxide film formed by thermal oxidation. The second insulating film 4 on the first electrode 3 is a silicon oxide film formed by PECVD. The first electrode 3 is a 0.05-µm-thick titanium electrode, and the second electrode 7 is a 0.1-μm-thick titanium electrode. The first membrane 6 and the second membrane 8 are each a silicon nitride film formed by PECVD and are formed to have a tensile stress of 100 MPa. The first membrane 6 and the second membrane 8 are 25 μm in diameter and are 0.3 μm and 0.5 μm, respectively, in thickness. The gap 12 is 0.2 μm in depth. The second electrode 7 has a diameter of 21 μm, which is smaller than that of the first membrane 6 and the second membrane 8. The second electrode 7 has a stress of 400 MPa. In the present configuration, the second electrode 7 is provided only in the area where the vibrating film 9 is displaced by a large amount for transmitting and receiving ultrasonic waves. This means that vibration of the vibrating film 9 can be converted to an electrical signal with high efficiency. If the second electrode 7 is formed over the entire surface of the vibrating film 9, the electrode at the edge of the vibrating film 9 forms a parasitic capacitance and increases noise. By making the diameter of the second electrode 7 smaller than that of the first membrane 6 and the second membrane 8, the transmission or reception sensitivity can be improved.

Each element 17 includes a plurality of cells 15. Etching holes for forming the gap 12 in each cell 15 of the element 17 are sealed with the sealing portions 14, which allow the stress in the gap 12 to be kept at 200 Pa. The thickness of the sealing portions 14 may be at least 2.7 times the depth of the gap 12, so that outside air can be prevented from entering the gap 12. In particular, since PECVD provides less conformal and less uniform deposition than low-pressure chemical vapor deposition (LPCVD), the thickness of the sealing portions 14 may be at least 2.7 times the depth of the gap 12. The sealing portions 14 are made by PECVD of silicon nitride, and the sealing layer for forming the sealing portions 14 is 0.6 μm in thickness. Because the sealing layer is removed, the sealing portions 14 are 0.8 μm in thickness.

In the capacitive transducer of Example 1, the second electrode 7 has the highest stress (tensile or compressive stress) among the first membrane 6, the second membrane 8, and the second electrode 7. The center plane of the vibrating film 9 including the first membrane 6, the second membrane 8, and the second electrode 7 is located at the center of the thickness of the vibrating film 9. The center plane of the second electrode 7 having the highest stress is located at the center of the thickness of the second electrode 7. Therefore, the center plane of the layer having the highest stress among the first membrane 6, the second membrane 8, and the second electrode 7 is located closer to the gap 12 than the center plane of the vibrating film 9 is to the gap 12. In this case, the maximum amount of deformation of the vibrating film 9 is 8 nm. For example, if the first membrane 6 and the second membrane 8 are 25 μm in diameter and are changed in thickness to 0.5 μm and 0.35 μm, respectively, the maximum amount of deformation of the vibrating film 9 is changed to 15 nm. With the present configuration, it is possible to reduce a difference in the amount of deformation in each vibrating film 9 caused by variation in thickness and stress of the first membrane 6, the second membrane 8, and the second electrode 7 included in the vibrating film 9. It is thus possible to reduce variation in frequency characteristics and transmission and reception sensitivity of the capacitive transducer.

Example 2

A method for manufacturing a capacitive transducer of Example 2 will now be described with reference to FIGS. 2A to 2H. A configuration of the capacitive transducer of Example 2 is substantially the same as that of Example 1. As illustrated in FIG. 2A, the first insulating film 22 is formed on the substrate 21. The substrate 21 is a silicon substrate. The first insulating film 22 on the substrate 21 is a 1-μm-thick silicon oxide film formed by thermal oxidation to provide insulation between the silicon substrate 21 and the first electrode 23. Next, the first electrode 23 is formed. The first electrode 23 is a 0.05-μm-thick titanium electrode. Then the second insulating film 24 is formed on the first electrode 23. The second insulating film 24 on the first electrode 23 is a silicon oxide film formed by PECVD.

Next, the sacrificial layer 25 is formed as illustrated in FIG. 2B. The sacrificial layer 25 is a 0.2-μm-thick chromium layer. With an etching solution for chromium, the vibrating film 29 made of silicon nitride and the second insulating film 24 made of silicon oxide and disposed on the first electrode 23 are etched much slower than the sacrificial layer 25 made of chromium. Therefore, the vibrating film 29 and the second insulating film 24 can be prevented from becoming thinner during removal of the chromium sacrificial layer 25, and desired thicknesses are achieved by film deposition alone.

Next, the first insulating layer 26 including the first membrane is formed as illustrated in FIG. 2C. The first insulating layer 26 is a silicon nitride layer formed by PECVD and having a tensile stress of 100 MPa or less. Then the second electrode 27 is formed. The second electrode 27 is a titanium electrode having a tensile stress of 400 MPa. Next, the second insulating layer 28 including the second membrane is formed. The second insulating layer 28 is a silicon nitride layer formed by PECVD and having a tensile stress of 100 MPa or less.

Next, as illustrated in FIG. 2D, the etching stop layer 30 is formed on the vibrating film 29 formed by deposition. The etching stop layer 30 is a 0.1-μm-thick silicon oxide layer formed by PECVD.

Next, the etching holes 31 are formed as illustrated in FIG. 2E. The etching holes 31 are holes for introducing an etching solution or gas for removing the sacrificial layer 25. The etching holes 31 can be easily formed by reactive ion etching (RIE) with fluorocarbon gas, or may be formed by wet etching. The etching holes 31 are 4 μm in diameter. Next, the sacrificial layer 25 is removed to form the gap 32. The sacrificial layer 25 is removed with an etching solution for chromium. A film having a compressive stress is used as the etching stop layer 30. The center plane of the metal layer having the highest stress among the first insulating layer 26, the second insulating layer 28, and the metal layer is located closer to the gap 32 than the center plane of the vibrating film 29 is to the gap 32. Therefore, since the amount of deformation of the structure composed of the vibrating film 29 and the etching stop layer 30 is small, sticking is less likely to occur.

Next, as illustrated in FIG. 2F, the sealing layer 33 is deposited to form the sealing portions 34 for sealing the etching holes 31. The sealing layer 33 is a silicon nitride layer formed by PECVD. Since the sealing layer 33 is deposited at a pressure of 200 Pa, the pressure in the gap 32 can be reduced. Also, since the vibrating film 29 is a silicon nitride film, a high degree of adhesion with the vibrating film 29 and a high level of airtightness in the gap 32 can be achieved.

Next, as illustrated in FIG. 2G, the sealing layer 33 is removed until the etching stop layer 30 is reached. The sealing layer 33 can be removed by dry etching, such as RIE or chemical dry etching (CDE). In CDE using a fluorocarbon gas, the silicon oxide forming the etching stop layer 30 is etched at an etching rate as low as about one-tenth of that at which the silicon nitride forming the sealing layer 33 is etched. Therefore, even when the sealing layer 33 is etched for a period of time longer than the time required for removing the sealing layer 33, the etching can be stopped at the etching stop layer 30.

Then, as illustrated in FIG. 2H, the etching stop layer 30 is removed. Only the etching stop layer 30 can be removed by etching the silicon oxide with a hydrofluoric acid. In another step (not shown), a wire connected to the first electrode 23 and the second electrode 27 is formed. The wire may be made of aluminum.

In the present method for manufacturing a capacitive transducer, where a sealing layer can be removed, a thin vibrating film can be obtained. The capacitive transducer including the thin vibrating film can have a very wide frequency band. The vibrating film can be formed by a deposition step alone. This means that it is easy to control the thickness of the vibrating film and possible to reduce variation in spring constant of the vibrating film or variation in deformation of the vibrating film caused by variation in thickness of the vibrating film. Therefore, it is possible to reduce variation in reception or transmission sensitivity among cells or elements.

Second Embodiment

A second embodiment of the present invention will now be described. In a capacitive transducer of the second embodiment, after a sealing layer is formed on an etching stop layer in the process of forming a vibrating film, the sealing layer is removed until the etching stop layer is reached. Here, the etching stop layer may be removed together with the sealing layer or may not be removed. Eventually, the vibrating film includes a first insulating film disposed to cover a gap and a second electrode disposed to overlap the gap in orthogonal projection onto a first electrode. The vibrating film may include the etching stop layer. A support portion of the vibrating film is disposed around the gap to support the vibrating film such that the vibrating film can vibrate. The support portion includes the sealing layer, has a thickness greater than that of the vibrating film, and has a layer structure different from that of the vibrating film. Since the sealing layer and the vibrating film are thus formed separately, it is possible to ensure reliable sealing of the gap with the sealing layer and make the vibrating film thinner. It is also possible to reduce variation in thickness of the vibrating film. The vibrating film can thus be formed in accordance with flexible design. A method for manufacturing a capacitive transducer involves forming a first insulating film on a sacrificial layer on a first electrode, the first insulating film forming at least part of a vibrating film; forming a etching stop layer on the first insulating film; forming an etching hole; and removing the sacrificial layer. The layer forming at least part of the vibrating film may be a layer other than the first insulating film, and may be designed on a case-by-case basis. Then after the sealing layer for sealing the etching hole is formed, at least part of the sealing layer overlapping the gap (i.e., portion which eventually becomes the vibrating film) is removed until the etching stop layer is reached, and the second electrode is formed on the etching stop layer or on the first insulating film. The second embodiment and examples of the present invention will now be described on the basis of the ideas described above. However, the present invention is not limited to the second embodiment and examples, and may be variously modified and changed within the scope of the gist of the present invention.

Figure 3A:
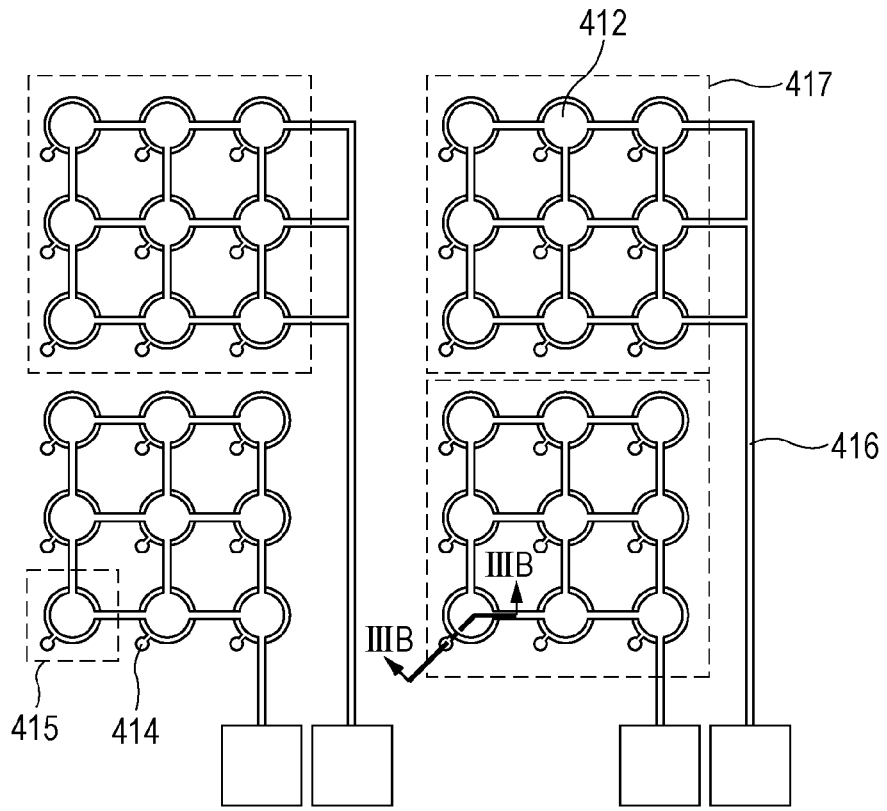
FIG. 3A is a top view of a capacitive transducer according to a second embodiment of the present invention.
Figure 3B:
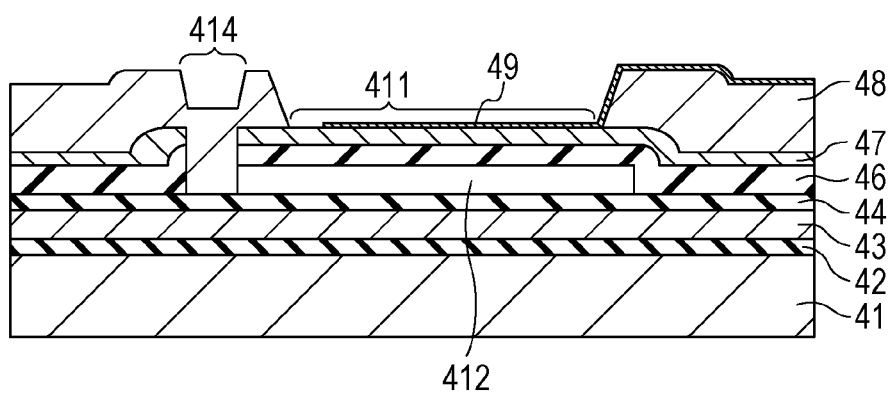
FIG. 3B is a cross-sectional view taken along line IIIB-IIIB of FIG. 3A.

The second embodiment of the present invention will be described with reference to FIGS. 3A and 3B and FIGS. 4A to 4K. FIG. 3A is a top view of the capacitive transducer according to the second embodiment. FIG. 3B is a cross-sectional view taken along line IIIB-IIIB of FIG. 3A. FIGS. 4A to 4K are cross-sectional views corresponding to FIG. 3B and illustrating steps of a method for manufacturing the capacitive transducer illustrated in FIGS. 3A and 3B.

The capacitive transducer according to the second embodiment has elements 417 each including a plurality of cells 415. Each element 417 includes nine cells 415 in FIG. 3A, but may include any number of cells. The capacitive transducer illustrated in FIG. 3A includes four elements 417, but may include any number of elements.

In each cell 415, a vibrating film 411 (see FIG. 3B) including a first insulating film 46 and a second electrode 49 disposed across a gap 412 from a first electrode 43 is supported to be able to vibrate. One of the first and second electrodes 43 and 49 is used as an electrode for applying a bias voltage, and the other is used as an electrode for applying or outputting an electrical signal. The first electrode 43 is used as an electrode for applying a bias voltage and the second electrode 49 is used as a signal output electrode in FIGS. 3A and 3B, but this may be reversed. The electrode for applying a bias voltage is common among the elements 417. The bias voltage may be common among the elements 417, but the signal output electrode needs to be electrically separated for each element 417.

A driving principle of the second embodiment will now be described. With a signal lead wire 416, the capacitive transducer can transmit an electrical signal from the second electrode 49. An electrical signal is transmitted through the signal lead wire 416 in the second embodiment, but may be transmitted through a through wire. An electrical signal is transmitted from the second electrode 49 in the second embodiment, but may be transmitted from the first electrode 43. For the capacitive transducer to receive ultrasonic waves, a voltage applying unit (not shown) applies a direct-current voltage to the first electrode 43 in advance. When ultrasonic waves are received, the vibrating film 411 including the second electrode 49 deforms. This changes the distance of the gap 412 between the second electrode 49 and the first electrode 43 and changes the capacitance therebetween. The change in capacitance causes current to flow through the signal lead wire 416. This current is converted by a current-to-voltage converter (not shown) to a voltage, so that ultrasonic waves can be received. The configuration of the signal lead wire 416 may be changed to apply a direct-current voltage to the second electrode 49 and output an electrical signal from the first electrode 43. When an alternating voltage is applied to the second electrode 49, the resulting electrostatic force causes the vibrating film 411 to vibrate. This allows transmission of ultrasonic waves. For transmission, the configuration of the signal lead wire 416 may be changed to apply an alternating voltage to the first electrode 43 and cause the vibrating film 411 to vibrate.

Figure 4A:
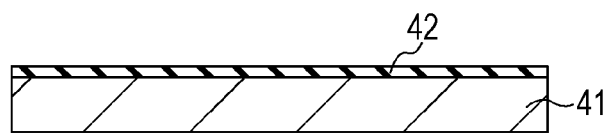
FIGS. 4A to 4K are cross-sectional views corresponding to FIG. 3B and illustrating a method for manufacturing the capacitive transducer illustrated in FIGS. 3A and 3B.

A method for manufacturing the capacitive transducer of the second embodiment will now be described. FIGS. 4A to 4K each correspond to the cross-sectional view taken along line IIIB-IIIB of FIG. 3A. As illustrated in FIG. 4A, an insulating film 42 is formed on a substrate 41. The insulating film 42 on the substrate 41 is provided for insulation between the substrate 41, such as a silicon substrate having conductivity, and the first electrode 43. If the substrate 41 is an insulating substrate, such as a glass substrate, the insulating film 42 on the substrate 41 may not be provided. The substrate 41 may be a substrate with small surface roughness. If the substrate 41 has large surface roughness, the surface roughness is transferred in the subsequent film deposition step, and causes variation in distance between the first electrode 43 and the second electrode 49 among cells 415 and elements 417. This variation leads to variation in transmission and reception sensitivity. Therefore, a substrate with small surface roughness may be used as the substrate 41.

Figure 4B:
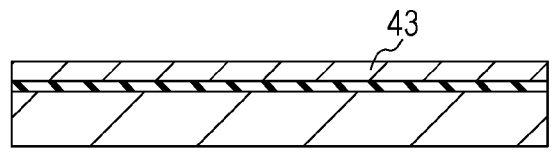

Next, the first electrode 43 is formed as illustrated in FIG. 4B. The first electrode 43 may be made of a conductive material, such as titanium or aluminum, that provides small surface roughness. As in the case of the substrate 41, if the first electrode 43 has large surface roughness, the surface roughness causes variation in distance between the first electrode 43 and the second electrode 49 among cells 415 and elements 417.

Figure 4C:
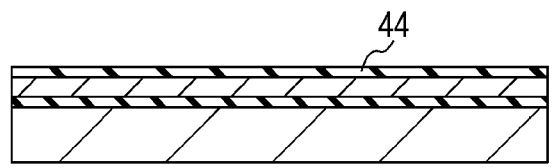

Next, as illustrated in FIG. 4C, an insulating film 44 is formed on the first electrode 43. The insulating film 44 on the first electrode 43 is formed to prevent an electrical short circuit or dielectric breakdown between the first electrode 43 and the second electrode 49 when a voltage is applied therebetween. The insulating film 44 also prevents the first electrode 43 from being etched in a sacrificial layer etching step (described below). When the first electrode 43 is resistant to the sacrificial layer etching step and is driven at a low voltage, the insulating film 44 on the first electrode 43 may not be provided, because the first insulating film 46 provides electrical insulation between the first electrode 43 and the second electrode 49. As in the case of the substrate 41, if the insulating film 44 has large surface roughness, the surface roughness causes variation in distance between the first electrode 43 and the second electrode 49 among cells 415 and elements 417. Therefore, the insulating film 44 may have small surface roughness. For example, the insulating film 44 may be a silicon nitride film or a silicon oxide film.

Figure 4D:
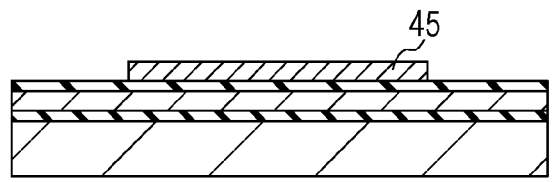

Next, a sacrificial layer 45 is formed as illustrated in FIG. 4D. The sacrificial layer 45 may be made of a material that provides small surface roughness. As in the case of the substrate 41, if the sacrificial layer 45 has large surface roughness, the surface roughness causes variation in distance between the first electrode 43 and the second electrode 49 among cells 415 and elements 417. To shorten the time of etching for removing the sacrificial layer 45, a material having a high etching rate may be used to form the sacrificial layer 45. When the sacrificial layer 45 is removed with an etching solution or gas, it is necessary that etching selectivity among materials around the sacrificial layer 45, the insulating film 44 on the first electrode 43, the first insulating film 46, and an etching stop layer 47 be sufficiently high.

Figure 4E:
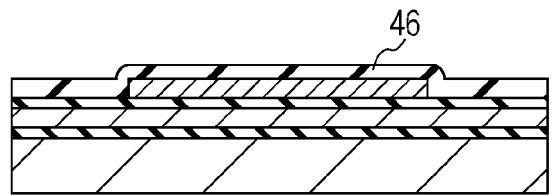
Figure 4F:
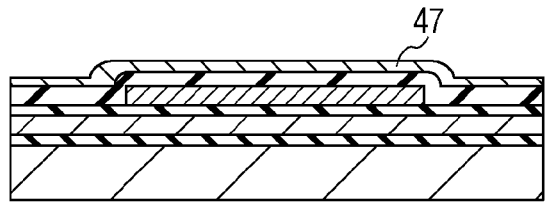

Next, the first insulating film 46 is formed as illustrated in FIG. 4E, and the etching stop layer 47 is formed as illustrated in FIG. 4F. The overall tensile stress of the first insulating film 46 and the etching stop layer 47 may be low. After the sacrificial layer removing step (described below), these two layers become a membrane supported on the gap 412. If the membrane has a compressive stress, the membrane may be significantly deformed by sticking or buckling in the sacrificial layer removing step. The sticking means that the membrane, which is a structure, adheres to a layer under the gap 412 after removal of the sacrificial layer 45. If the tensile stress is too large, the stress tends to cause the membrane to be broken, for example, by cracks. The etching stop layer 47 may eventually remain and form part of the vibrating film 411, or may be removed from a portion to be the vibrating film 411 later on.

When the etching stop layer 47 is left as part of the vibrating film 411, the etching rate of the etching stop layer 47 needs to be sufficiently low with respect to etching conditions for a sealing layer 48. The lower the etching rate of the etching stop layer 47 as compared to that of the sealing layer 48, the better and the thinner the etching stop layer 47. When the etching stop layer 47 is removed at the position to be the vibrating film 411, it is necessary that the etching selectivity between the etching stop layer 47 and the first insulating film 46 under the etching stop layer 47 be sufficiently high in the removal (etching) step. An exemplary combination of the first insulating film 46 and the etching stop layer 47 may be a silicon nitride film whose tensile stress is controllable and a silicon oxide film having etching selectivity with respect to the silicon nitride film. Note that the silicon nitride film and the silicon oxide film correspond to the first insulating film 46 and the etching stop layer 47, respectively.

Figure 4G:
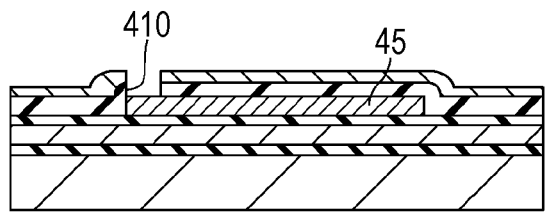
Figure 4H:
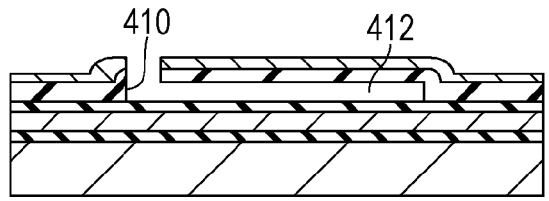

Next, an etching hole 410 is formed as illustrated in FIG. 4G. The etching hole 410 is a hole for introducing an etching solution or gas for removing the sacrificial layer 45. The etching hole 410 is formed to pass through the etching stop layer 47 and the first insulating film 46 and reach the sacrificial layer 45. Next, as illustrated in FIG. 4H, the sacrificial layer 45 is removed through the etching hole 410 by means of wet etching or isotropic dry etching, so as to form the gap 412.

Figure 4I:
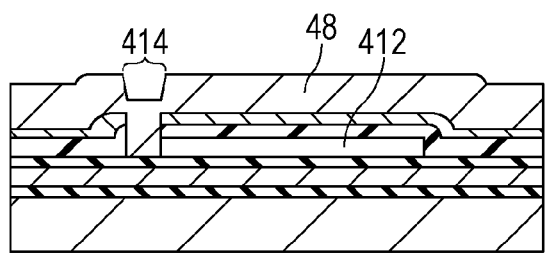

Next, as illustrated in FIG. 4I, the sealing layer 48 is formed to seal the etching hole 410. A sealing portion 414 is configured to prevent entry of liquid and outside air into the gap 412. Sealing the etching hole 410 allows the capacitive transducer to be used in liquid. To achieve sufficient sealing, the sealing layer 48 needs to be sufficiently thicker than the gap 412. Since the sealing layer 48 over the gap 412 is removed later on in the present invention, the sealing layer 48 may have a sufficient thickness for better sealing.

Figure 4J:
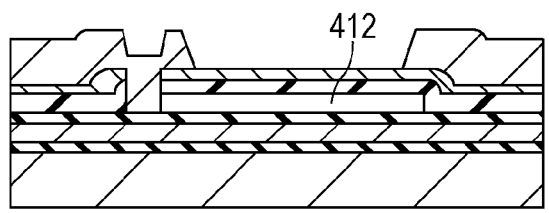

Next, as illustrated in FIG. 4J, the sealing layer 48 is removed, only at a position corresponding to the gap 412, by etching until the etching stop layer 47 is reached. More technically, at least part of the sealing layer 48 overlapping the gap 412 in orthogonal projection of the sealing layer 48 onto the first electrode 43 is removed. When the etching stop layer 47 is made of a material having an etching rate sufficiently low with respect to etching conditions for the sealing layer 48, even if the etching rate of the sealing layer 48 varies in the substrate 41, the thickness of the eventually remaining part of the sealing layer 48 can be almost defined by the total thickness of the first insulating film 46 and the etching stop layer 47.

Figure 4K:
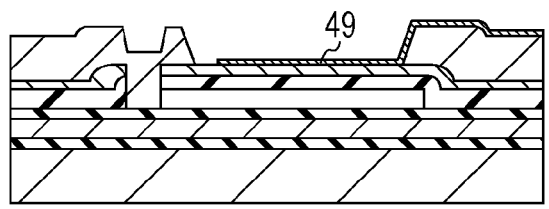

Next, the second electrode 49 is formed as illustrated in FIG. 4K. The second electrode 49 forms part of the vibrating film 411 of the capacitive transducer together with the first insulating film 46 and the etching stop layer 47. The vibrating film 411 may be thinner for better characteristics of the capacitive transducer. Therefore, the second electrode 49 may also be sufficiently thin, as long as satisfactory electrical characteristics are achieved. The second electrode 49 may be made of a generally used conductive material. The configuration of the capacitive transducer according to the second embodiment is thus obtained. In the second embodiment, where the sealing layer 48 can be removed at the position corresponding to the gap 412, the thickness of the vibrating film 411 can be controlled independently of that of the sealing layer 48. Although this facilitates forming a thin vibrating film, it is still possible to form a thick vibrating film. Also, the thickness of the vibrating film 411 is not affected by variation in etching rate, and variation in thickness can be reduced. Therefore, it is possible to obtain a good capacitive transducer having a wide frequency band and less variation in reception or transmission sensitivity among cells or elements. In the configuration of the second embodiment, the sealing layer 48 having a large thickness is left unremoved, except at the position of the vibrating film 411 corresponding to the gap 412. Therefore, the first electrode 43 and the second electrode 49 are distant from each other, except in the area corresponding to the vibrating film 411. That is, the distance between the first electrode 43 and the second electrode 49 is small in the area corresponding to the vibrating film 411 where actually the capacitive transducer actively works, whereas the distance between the first electrode 43 and the second electrode 49 is large in the other area. This means that the capacitive transducer has a large active capacitance and a small parasitic capacitance, and that a large signal-to-noise (S/N) ratio can be achieved in receiving operation of the capacitive transducer.

Additionally, since the distance between the first electrode 43 and the second electrode 49 is large and the insulating film thickness is large in the area other than the area corresponding to the gap 412, it is possible to obtain a capacitive transducer which has good voltage resistance and is less prone to dielectric breakdown even if a large voltage is applied between the first electrode 43 and the second electrode 49. To protect the capacitive transducer of the second embodiment from liquid and contact during use, a resin layer (not shown) which is less affected by vibration may be added, as an upper layer of the capacitive transducer, to the structure illustrated in the cross-sectional view of FIG. 3B.

Japanese Patent Laid-Open No. 2008-98697 also describes a capacitive transducer that has a small parasitic capacitance and good voltage resistance because of the fact that the insulating film thickness between upper and lower electrodes in a portion to serve as a vibrating film differs from that in the other portion. However, the second embodiment of the present invention provides the capacitive transducer having a small parasitic capacitance and good voltage resistance by using another configuration. The capacitive transducer of the second embodiment has not only a small parasitic capacitance and good voltage resistance, but also has a thin vibrating film with a uniform thickness.

The second embodiment will be described in detail using concrete examples.

Example 3

Example 3 will be described with reference to FIGS. 3A and 3B and FIGS. 4A to 4K. The capacitive transducer of Example 3 has elements 417 each including a plurality of cells 415. Each element 417 includes nine cells 415 in FIG. 3A, but may include any number of cells. The capacitive transducer illustrated in FIG. 3A includes four elements 417, but may include any number of elements. In each cell 415, the vibrating film 411 including the second electrode 49 disposed across the gap 412 from the first electrode 43 is supported to be able to vibrate. In Example 3, the vibrating film 411 includes the first insulating film 46, the etching stop layer 47, and the second electrode 49. The first electrode 43 serves as an electrode for applying a bias voltage, and the second electrode 49 serves as a signal output electrode. Although the vibrating film 411 of Example 3 is circular in shape, it may be rectangular or hexagonal in shape. In the case of a circular shape, the vibrating film 411 vibrates in an axisymmetric vibration mode. It is thus possible to reduce vibration of the vibrating film 411 in an unnecessary vibration mode.

In the method for manufacturing the capacitive transducer in Example 3, a silicon substrate is used as the substrate 41 illustrated in FIG. 4A. As the insulating film 42 on the silicon substrate 41, a silicon oxide film is formed to a thickness of 1 μm by thermal oxidation. Next, as illustrated in FIG. 4B, a titanium layer serving as the first electrode 43 is deposited to a thickness of 50 nm by sputtering, and then is patterned by photolithography and etching into a planar shape appropriate for the first electrode 43 of the capacitive transducer. Next, as illustrated in FIG. 4C, as the insulating film 44 on the first electrode 43, a silicon oxide film is deposited to a thickness of 100 nm by PECVD.

Next, a chromium layer is deposited to a thickness of 200 nm by sputtering, and is patterned by photolithography and etching into the sacrificial layer 45 (see FIG. 4D) which is to serve as the gap 412. The pattern of the sacrificial layer 45 is aligned to the pattern of the first electrode 43 previously formed. The sacrificial layer 45 is basically circular in shape to fit the shape of the cell 415, and a portion to be coupled to the etching hole 410 for removing the sacrificial layer 45 is added to the basic circular shape of the sacrificial layer 45. The diameter of the circular sacrificial layer 45 is 33 μm. Next, as illustrated in FIG. 4E, a silicon nitride film to serve as the first insulating film 46 is deposited to a thickness of 400 nm by PECVD. Conditions for depositing the silicon nitride film are adjusted such that the first insulating film 46 over the silicon substrate 41 has a tensile stress of about 100 MPa.

Next, as the etching stop layer 47 illustrated in FIG. 4F, a silicon oxide film is deposited to a thickness of 50 nm by PECVD. Next, as illustrated in FIG. 4G, the silicon oxide film serving as the etching stop layer 47 and the silicon nitride film serving as the first insulating film 46 are continuously etched in this order by photolithography and RIE. Then, the etching hole 410 is formed until the chromium layer serving as the sacrificial layer 45 is reached. The etching hole 410 is about 5 μm in diameter. The substrate 41 having the etching hole 410 is immersed into an etching solution for chromium (i.e., a mixture of ammonium cerium (IV) nitrate and perchloric acid) to remove the sacrificial layer 45. Thus, the sacrificial layer 45 is removed to form the gap 412 as illustrated in FIG. 4H. For drying, the etching solution is sequentially replaced with a liquid having a smaller surface tension in the following order: etching solution, water, isopropyl alcohol (IPA), and hydro fluoro ether (HFE). This is to prevent a phenomenon called sticking caused by the surface tension of the liquid. The sticking is adhesion of a portion to serve as the vibrating film 411 to a surface facing the gap 412. Next, a silicon nitride film is deposited to a thickness of 700 nm by PECVD to form the sealing layer 48 as illustrated in FIG. 4I, so as to seal the etching hole 410 with the sealing portion 414.

Next, by using photolithography, an etching mask pattern is formed with a resist partially exposed only above the gap 412. Then the silicon nitride film serving as the sealing layer 48 above the gap 12 is removed by CDE which uses a mixture of carbon tetrafluoride and oxygen as an etching gas. In this etching technique, the etching selectivity ratio of the silicon nitride film serving as the sealing layer 48 to the silicon oxide film serving as the etching stop layer 47 (i.e., "etching rate of silicon nitride"/"etching rate of silicon oxide") is as large as 50 or more. Therefore, even if the silicon nitride film serving as the sealing layer 48 is over-etched, the thickness of the etching stop layer 47 changes only a little. Thus as illustrated in FIG. 4J, the sealing layer 48 is removed only in the area corresponding to the gap 412.

Then as illustrated in FIG. 4K, a titanium layer is deposited to a thickness of 50 nm as the second electrode 49 and patterned appropriately for the second electrode 49. The second electrode 49 in the cell 415 is 29 μm in diameter.

In the present configuration, the second electrode 49 is provided only in the area where the vibrating film 411 is displaced by a large amount for transmitting and receiving ultrasonic waves. This means that vibration of the vibrating film 411 can be converted to an electrical signal with high efficiency. If the second electrode 49 is formed over the entire surface of the vibrating film 411, the electrode at the edge of the vibrating film 411 forms a parasitic capacitance and tends to increase noise. To prevent this, the diameter of the second electrode 49 is made smaller than that of the first insulating film 46, so that the transmission or reception sensitivity can be improved. Each element 417 includes a plurality of cells 415. The etching hole 410 for forming the gap 412 in each cell 415 of the element 417 is sealed with the sealing portion 414. For example, by adding the signal lead wire 416 electrically connected to the first electrode 43 and the second electrode 49 as illustrated in FIG. 3A, the resulting device can be used as a capacitive transducer.

In the capacitive transducer of Example 3, the vibrating film 411 includes the first insulating film 46, the etching stop layer 47, and the second electrode 49. The thickness of the vibrating film 411 can be controlled independently of that of the sealing layer 48. Therefore, the vibrating film 411 can be made much thinner than in the case where the vibrating film 411 includes the sealing layer 48, and the resulting device is suitable for use as a capacitive transducer with wideband characteristics. Variation in thickness of the vibrating film 411 is less likely to be affected by variation in etching of the sealing layer 48, and is determined only by variation in forming the first insulating film 46, the etching stop layer 47, and the second electrode 49. Therefore, variation in overall film thickness among cells 415 and elements 417 is small, and a transducer with small variation in frequency characteristics and transmission and reception sensitivity can be obtained. Also, since the first electrode 43 and the second electrode 49 are distant from each other and the parasitic capacitance is small, except in the area corresponding to the gap 412, reception characteristics with a large S/N ratio can be achieved and a capacitive transducer having a high withstanding voltage can be obtained.

Example 4

Figure 5A:
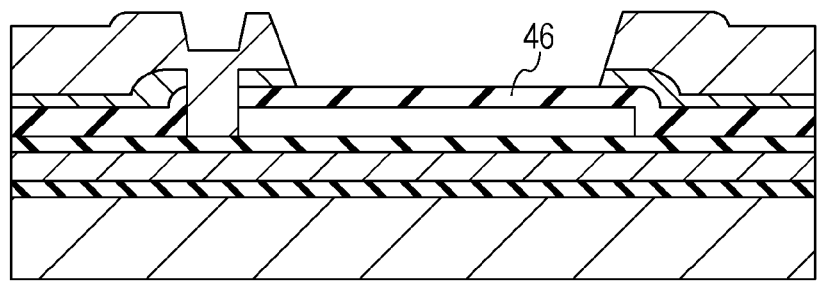
FIGS. 5A and 5B are cross-sectional views illustrating a variation to the capacitive transducer of FIGS. 3A and 3B.

Example 4 will now be described. A capacitive transducer is made in the same manner as in Example 3 until removal of part of the sealing layer 48 corresponding to the gap 412 (see FIG. 4J). In Example 4, however, the silicon oxide film serving as the etching stop layer 47 above the gap 412 is removed by immersion in buffered hydrofluoric acid for a short time to reach the state of FIG. 5A. Silicon oxide and silicon nitride are very different in etching rate with respect to buffered hydrofluoric acid. Therefore, in short-term immersion, only the silicon oxide film serving as the etching stop layer 47 is removed and most of the silicon nitride film serving as the first insulating film 46 is left unetched.

Figure 5B:
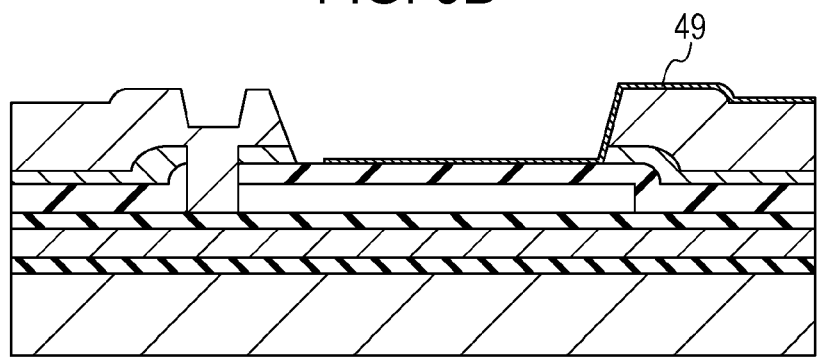

Then as in Example 3, a titanium layer is deposited to a thickness of 50 nm as the second electrode 49 and patterned appropriately for the second electrode 49. The capacitive transducer having the configuration illustrated in FIG. 5B is thus obtained. In this configuration, where the vibrating film 411 includes the first insulating film 46 and the second electrode 49, a thinner vibrating film can be produced and the resulting capacitive transducer can be suitably used as a wideband capacitive transducer. As in Example 3, reception characteristics with a large S/N ratio and a high withstanding voltage can be achieved.

Example 5

Example 5 will now be described. A capacitive transducer is made in the same manner as in Example 3 until deposition of the sealing layer 48 (see FIG. 4I). In the subsequent step of patterning the sealing layer 48, an exposure mask different from that in Example 3 is used in photolithography. In some cells in each element 417, a portion of the sealing layer 48 above the gap 412 is removed as in Example 3, whereas in the other cells, the portion of the sealing layer 48 above the gap 412 is left unremoved.

Figure 6A:
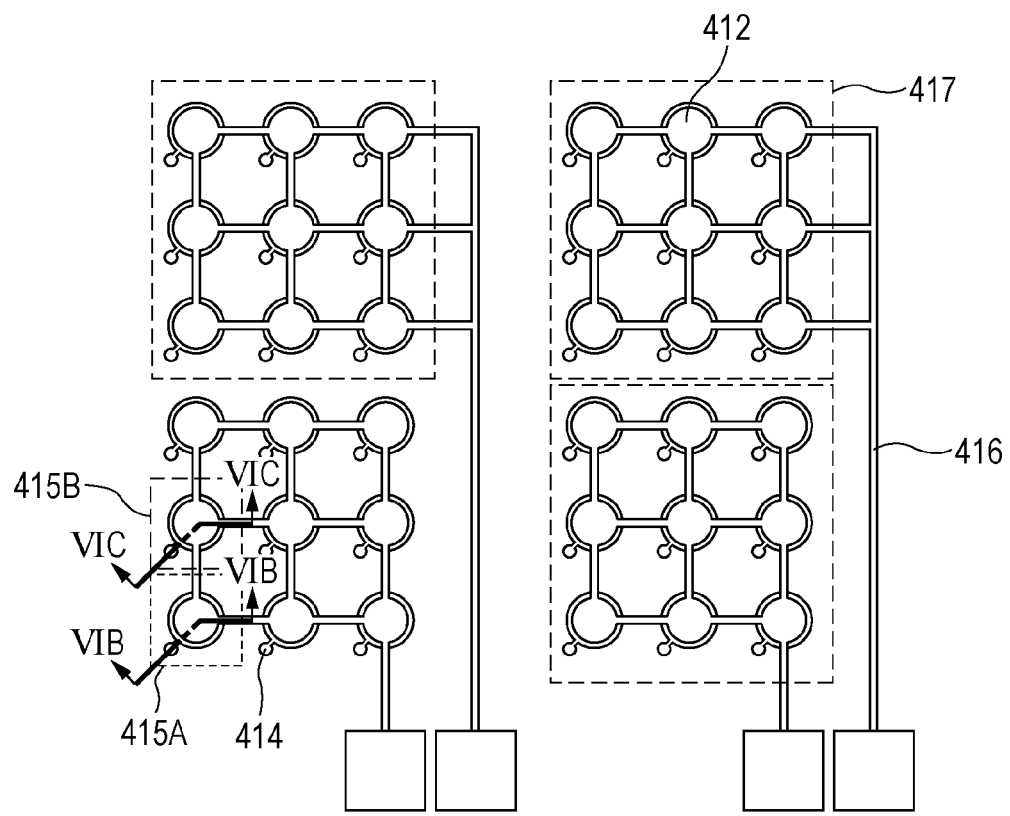
FIG. 6A is a top view of a variation to the capacitive transducer of FIGS. 3A and 3B.
Figure 6B:
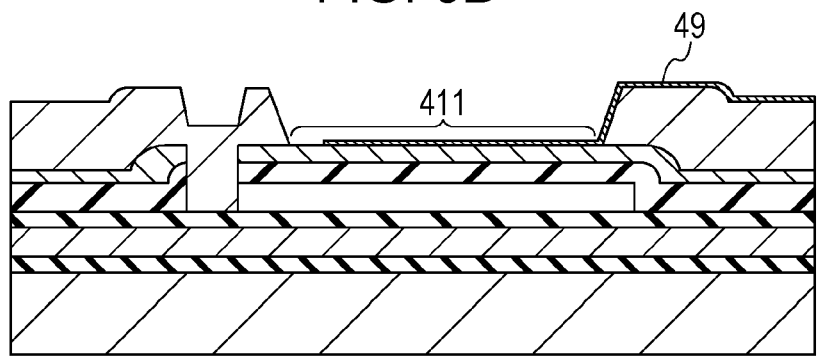
FIG. 6B is a cross-sectional view taken along line VIB-VIB of FIG. 6A.
Figure 6C:
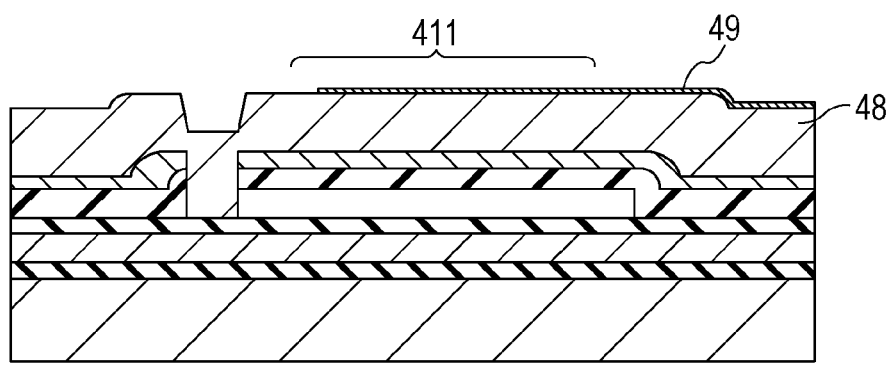
FIG. 6C is a cross-sectional view taken along line VIC-VIC of FIG. 6A.

The other steps are performed in the same manner as in Example 3. Eventually, as illustrated in FIGS. 6A to 6C, a capacitive transducer having a plurality of elements 417 each including both cells 415A and 415B is obtained. FIGS. 6B and 6C correspond to the cells 415A and 415B, respectively, in FIG. 6A. The capacitive transducer actually includes many cells 415A and 415B, not one cell 415A and one cell 415B. This capacitive transducer includes cells 417 having respective vibrating films 411 with different spring constants. That is, the capacitive transducer includes cells 417 having different proper frequency bands, and thus can achieve wide frequency band characteristics.

Other Embodiments

The capacitive transducer described above is applicable to a subject information acquiring apparatus, such as an ultrasonic diagnostic apparatus. The subject information acquiring apparatus receives acoustic waves from a subject at the capacitive transducer, and uses output electrical signals to acquire subject information which reflects optical characteristic values of the subject, such as light absorption coefficients, or subject information which reflects differences in acoustic impedance.

Specifically, an information acquiring apparatus irradiates a subject with light (electromagnetic waves including visible light and infrared light). Then, the information acquiring apparatus receives photoacoustic waves generated at a plurality of points (areas) in the subject, and acquires a characteristic distribution representing a distribution of characteristic information corresponding to the plurality of points in the subject. The characteristic information acquired through the photoacoustic waves refers to characteristic information related to absorption of light. The characteristic information includes one that reflects an initial sound pressure of photoacoustic waves generated by light irradiation, a light energy absorption density derived from the initial sound pressure, an absorption coefficient, or concentrations of substances contained in tissues. The concentrations of substances are, for example, oxygen saturation, total hemoglobin concentration, and oxyhemoglobin or deoxyhemoglobin concentration. The information acquiring apparatus may be used for the purpose of diagnosis of malignant tumors or blood vessel diseases of humans or other animals, or follow-up of chemotherapy. Therefore, examples of the subject may include diagnostic objects, such as breasts, necks, and abdomens, of living bodies, such as humans and other animals. The subject includes a light absorber formed by tissues having relatively high absorption coefficients in the subject. For example, if the subject is part of a human body, the light absorber may be oxyhemoglobin, deoxyhemoglobin, blood vessel including many oxyhemoglobins and deoxyhemoglobins, tumor including many newborn blood vessels, or plaque in carotid artery walls. A molecular probe specifically bound to malignant tumors using gold particles or graphite, or a capsule for delivering drugs may also serve as a light absorber.

By receiving not only photoacoustic waves, but also reflected ultrasonic echo waves obtained by reflection of ultrasonic waves in the subject, the ultrasonic waves being transmitted from a probe including a transducer, an acoustic characteristic distribution in the subject can be acquired. The acoustic characteristic distribution includes a distribution that reflects differences in the acoustic impedance of tissues in the subject.

Figure 7A:
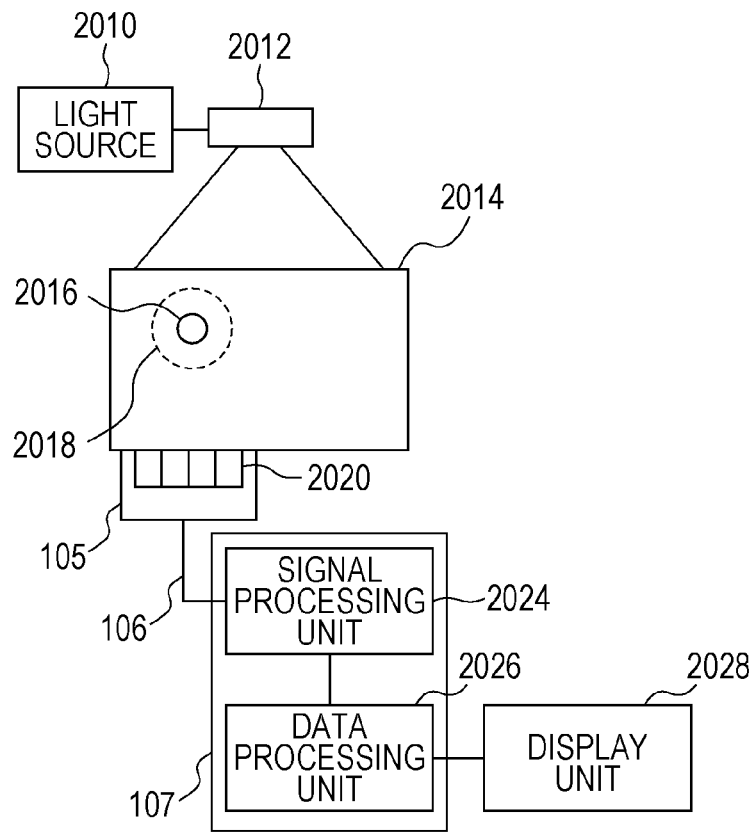
FIGS. 7A and 7B each illustrate an information acquiring apparatus including a capacitive transducer.

FIG. 7A illustrates an information acquiring apparatus using a photoacoustic effect. Pulsed light from a light source 2010 is applied through an optical member 2012, such as a lens, a mirror, or an optical fiber, to a subject 2014. A light absorber 2016 in the subject 2014 absorbs energy of the pulsed light and generates photoacoustic waves 2018 which are acoustic waves. In a probe unit 105, a transducer 2020, as described, receives the photoacoustic waves 2018, converts them to electrical signals, and outputs the electrical signals to a front-end circuit of the probe unit 105. In the front-end circuit, the electrical signals are processed by a preamplifier. The processed electrical signals are transmitted through a connecting portion 106 to a signal processing unit 2024 of a main body 107. The signal processing unit 2024 performs signal processing, including analog-to-digital (A/D) conversion and amplification, on the input electrical signals, and outputs the processed electrical signals to a data processing unit 2026 of the main body 107. The data processing unit 2026 uses the input signals to acquire subject information (characteristic information which reflects optical characteristic values of the subject 2014, such as light absorption coefficients) as image data. Here, the signal processing unit 2024 and the data processing unit 2026 are collectively referred to as an image processor. A display unit 2028 displays an image on the basis of image data input from the data processing unit 2026.

Figure 7B:
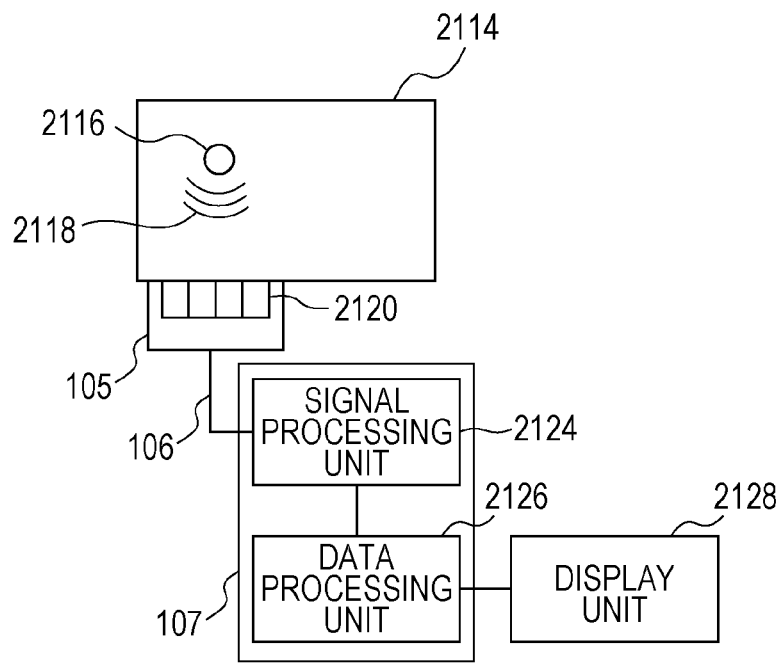

FIG. 7B illustrates an information acquiring apparatus, such as an ultrasonographic diagnostic apparatus, using reflection of acoustic waves. Acoustic waves transmitted from a transducer 2120, as described, in a probe unit 105 to a subject 2114 are reflected by a reflector 2116. The transducer 2120 receives reflected acoustic waves (reflected waves) 2118, converts them to electrical signals, and outputs the electrical signals to a front-end circuit of the probe unit 105. In the front-end circuit, the electrical signals are processed by a preamplifier. The processed electrical signals are transmitted through a connecting portion 106 to a signal processing unit 2124 of a main body 107. The signal processing unit 2124 performs signal processing, including A/D conversion and amplification, on the input electrical signals, and outputs the processed electrical signals to a data processing unit 2126 of the main body 107. The data processing unit 2126 uses the input signals to acquire subject information (characteristic information which reflects differences in acoustic impedance) as image data. Again, the signal processing unit 2124 and the data processing unit 2126 are collectively referred to as an image processor. A display unit 2128 displays an image on the basis of image data input from the data processing unit 2126.

The probe unit 105 may be either configured to mechanically scan the subject, or may be hand-held and moved by a user, such as a physician or technician, with respect to the subject. In the case of an apparatus using reflected waves, such as that illustrated in FIG. 7B, a probe for transmitting acoustic waves may be provided separately from that for receiving reflected waves. An apparatus configured to have both functions of the apparatuses illustrated in FIGS. 7A and 7B may also be provided. This apparatus acquires not only subject information reflecting optical characteristic values of the subject, but also acquires subject information reflecting differences in acoustic impedance. In this case, the transducer 2020 in FIG. 7A may be configured not only to receive photoacoustic waves, but also to transmit acoustic waves and receive reflected waves.

In a method for manufacturing a capacitive transducer as described above, a thin vibrating film can be provided by removing a sealing layer. Before the step of forming the sealing layer, an etching stop layer is formed on a layer forming at least part of the vibrating film. Thus, in a film deposition step, the thickness of the vibrating film can be easily defined at high yields. Therefore, it is possible to reduce variation in thickness of the vibrating film caused by variation in etching rate in a substrate that occurs when the sealing layer deposited on the vibrating film is removed, and thus to reduce variation in frequency characteristics and transmission and reception sensitivity of the capacitive transducer.

In the capacitive transducer as described in the above examples, the amount of deformation of the vibrating film is small, because a center plane of a layer having the highest stress among a first membrane, a second membrane, and a second electrode is located closer to a gap (first electrode) than a center plane of the vibrating film is to the gap. With this configuration, it is possible to reduce a difference in the amount of deformation in each vibrating film caused by variation in thickness and stress of the first membrane, the second membrane, and the second electrode included in the vibrating film. It is thus possible to reduce variation in frequency characteristics and transmission and reception sensitivity of the capacitive transducer.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-173190 filed Aug. 23, 2013 and No. 2013-185796 filed Sep. 8, 2013, which are hereby incorporated by reference herein in their entirety.

What is claimed is:

1. A method for manufacturing a capacitive transducer including a cell having a structure in which a vibrating film including a second electrode disposed across a gap from a first electrode is supported to be able to vibrate, the method comprising the steps of:
   forming an insulating layer on the first electrode;
   forming a sacrificial layer on the insulating layer;
   forming a layer on the sacrificial layer, the layer forming at least part of the vibrating film;
   forming an etching hole to communicate with the sacrificial layer;
   removing the sacrificial layer;
   forming a sealing layer for sealing the etching hole; and
   etching at least part of the sealing layer,
   wherein before the step of removing the sacrificial layer, an etching stop layer is formed on the layer forming at least part of the vibrating film; and in the step of etching at least part of the sealing layer, the at least part of the sealing layer is removed until the etching stop layer is reached.

2. The method according to claim 1, wherein the vibrating film includes a first membrane and a second membrane disposed with the second electrode interposed therebetween; and the step of forming the layer forming at least part of the vibrating film includes forming a first insulating layer including the first membrane on the sacrificial layer, forming a metal layer including the second electrode, and forming a second insulating layer including the second membrane.

3. The method according to claim 2, wherein in the step of forming the layer forming at least part of the vibrating film, the center plane of the layer having the highest stress among the first insulating layer, the second insulating layer, and the metal layer is made closer to the gap than a center plane of the vibrating film is to the gap.

4. The method according to claim 1, wherein the vibrating film is formed to have a tensile stress, and the etching stop layer is formed to have a compressive stress.

5. The method according to claim 1, wherein the step of etching part of the sealing layer is followed by removing the etching stop layer.

6. The method according to claim 1, wherein the etching stop layer is not removed.

7. The method according to claim 1, wherein in the step of forming the sealing layer for sealing the etching hole, the sealing layer is formed by plasma-enhanced chemical vapor deposition.

8. The method according to claim 1, wherein an insulating film is formed as the layer forming at least part of the vibrating film; and in the step of etching part of the sealing layer, at least part of the portion of the sealing layer overlapping the gap in orthogonal projection of the sealing layer onto the first electrode, is removed until the etching stop layer is reached, the method further comprising the step of forming, in the at least part of the portion overlapping the gap, the second electrode on the etching stop layer or on the insulating film.

9. The method according to claim 8, wherein at least part of the portion of the etching stop layer overlapping the gap in orthogonal projection of the etching stop layer onto the first electrode is removed.

10. The method according to claim 8, wherein the etching stop layer is an insulating layer.

11. The method according to claim 8, wherein the insulating film and the sealing layer are made of silicon nitride, and the etching stop layer is made of silicon oxide.

12. The method according to claim 1, wherein the etching hole are formed to extend through the etching stop layer.

13. The method according to claim 1, wherein a material used to form the sealing layer is the same as a material used to form the vibrating film.

14. The method according to claim 1, wherein the step of etching at least part of the sealing layer, the sealing layer on the etching stop layer is completely etched away.

15. The method according to claim 1, wherein the etching hole passes through the etching stop layer and the layer forming at least part of the vibrating film.

* * * * *